United States Patent [19]

Kume et al.

[11] Patent Number: 4,909,828
[45] Date of Patent: Mar. 20, 1990

[54] HERBICIDALLY ACTIVE 2,5-DIHYDROPYRROLES

[75] Inventors: Toyohiko Kume, Hinio; Toshio Goto, Machida; Atsumi Kamochi, Hino; Akihiko Yanagi, Oume; Hiroshi Miyauchi, Hachioji, all of Japan

[73] Assignee: Nihon Tokushu Noyaku Seizo K.K., Tokyo, Japan

[21] Appl. No.: 337,495

[22] Filed: Apr. 13, 1989

[30] Foreign Application Priority Data

Apr. 27, 1988 [JP] Japan ................. 63-102445

[51] Int. Cl.$^4$ ................. A01N 43/76; A01N 43/82; C07D 403/04; C07D 413/04
[52] U.S. Cl. ......................... 71/92; 71/88; 71/95; 548/143; 548/233
[58] Field of Search ............... 548/143, 233; 71/88, 71/92, 95

[56] References Cited

U.S. PATENT DOCUMENTS 4,138,243  2/1979  Bohner et al. ................ 548/195
4,220,655  9/1980  Bohner et al. ................ 548/195

FOREIGN PATENT DOCUMENTS 2735841  2/1978  Fed. Rep. of Germany .
2400013  3/1979  France .
633678  12/1982  Switzerland .

OTHER PUBLICATIONS

Boehner et al., Chem. Abst. 88-152415u (1978), eq. JP 23965/1978.

Primary Examiner—Mukund J. Shah
Assistant Examiner—Cecilia Shen
Attorney, Agent, or Firm—Sprung Horn Kramer & Woods

[57] ABSTRACT

Herbicidal 2,5-dihydropyrroles of the formula

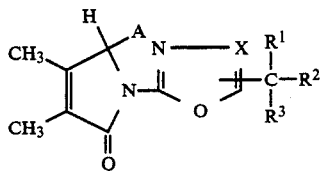

(I)

wherein
A represents hydroxy, halogen, an alkylcarbonyloxy group having alkyl with 1 to 4 carbon atoms optionally substituted by halogen, or an alkylsulfonyloxy group having 1 to 4 carbon atoms optionally substituted by halogen,
X represents CH or N, and
$R^1$, $R^2$ and $R^3$ each represent hydrogen, or an alkyl group having 1 to 4 carbon atoms optionally substituted by halogen, with the proviso that all of $R^1$, $R^2$ and $R^3$ do not simultaneously represent hydrogen,
or $R^2$ and $R^3$, together with the carbon atom to which they are bonded, may form an alicyclic ring with 3 to 6 carbon atoms.

Intermediates of the formula

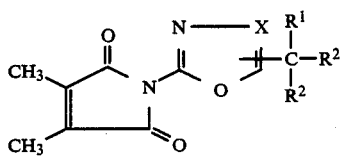

(II)

are also new.

11 Claims, No Drawings

HERBICIDALLY ACTIVE 2,5-DIHYDROPYRROLES

The present invention relates to novel 2,5-dihydropyrroles, to processes and novel intermediates for their preparation and to their use as herbicides.

It has already been disclosed that certain 2,5-dihydropyrroles are active in controlling plants and animal pests (see Japanese Patent Laid-open 23965/1978)

There have now been found novel 2,5-dihydropyrroles of the formula (I)

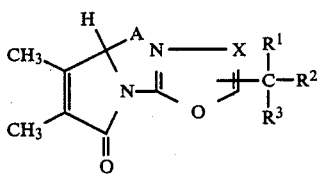

wherein
- A represents hydroxy, halogen, an alkylcarbonyloxy group having alkyl with 1 to 4 carbon atoms optionally substituted by halogen, or an alkylsulfonyloxy group having 1 to 4 carbon atoms optionally substituted by halogen,
- X represents CH or N, and
- $R^1$, $R^2$ and $R^3$ each represent hydrogen, or an alkyl group having 1 to 4 carbon atoms optionally substituted by halogen, with the proviso that all of $R^1$, $R^2$ and $R^3$ do not simultaneously represent hydrogen,
- or $R^2$ and $R^3$, together with the carbon atom to which they are bonded, may form an alicyclic ring with 3 to 6 carbon atoms.

The compounds of the formula (I) can be obtained by a process in which,
(a) in the case where A represents hydroxy; compounds of the formula (II)

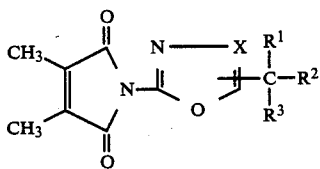

wherein X, $R^1$, $R^2$ and $R^3$ are respectively the same as above, are reacted with a reducing agent in the presence of inert solvents, or (b) in the case where A represents halogen; compounds of the formula (Ia)

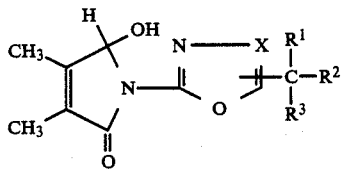

wherein X, $R^1$, $R^2$ and $R^3$ are respectively the same as above, are reacted with a halogenating agent in the presence of inert solvents, or (c) in the case where A represents an alkylcarbonyloxy group having alkyl with 1 to 4 carbon atoms optionally substituted by halogen or an alkylsulfonyloxy group with 1 to 4 carbon atoms optionally substituted by halogen, then A is replaced by —O—W,
the compounds of the aforementioned formula (Ia) are reacted with compounds of the formula (III)

$$W-M \qquad (III)$$

wherein W represents an alkylcarbonyl group having alkyl with 1 to 4 carbon atoms optionally substituted with halogen, or represents an alkylsulfonyl group with 1 to 4 carbon atoms optionally substituted by halogen, and M represents halogen, or compounds of the formula (IV)

$$W-O-W \qquad (IV)$$

wherein W is the same as above, in the presence of inert solvents and if appropriate in the presence of a base.

The 2,5-dihydropyrroles of the formula (I) according to the invention exhibit a strong herbicidal action.

The 2,5-dihydropyrroles of the formula (I) are novel, although generically embraced by the aforementioned Japanese Patent Laid-open 23965/1978

Surprisingly, the 2,5-dihydropyrroles according to the invention exhibit a substantially greater selective herbicidal action than those known from the prior art, Japanese Patent Laid-open No. 23965/1978, and at the same time, have good compatibility to crops.

Among the 2,5-dihydropyrroles according to the invention, of the formula (I), preferred compounds are those in which A represents hydroxy, chlorine, bromine, an alkylcarbonyloxy having alkyl with 1 or 2 carbon atoms optionally substituted by fluorine and/or by chlorine, or an alkylsulfonyloxy having 1 or 2 carbon atoms optionally substituted by fluorine and/or by chlorine, X represents CH or N, $R^1$ represents methyl or ethyl, and $R^2$ and $R^3$ each represent methyl, ethyl, or chlorine- or fluorine-substituted alkyl with 1 or 2 carbon atoms, or $R^2$ and $R^3$, together with the carbon atom to which they are bonded, may form a cyclopropane ring.

Very particularly preferred 2,5-dihydropyrroles of the formula (I) are those in which A represents hydroxy, chlorine, bromine, acetyloxy, trifluoroacetyloxy or methylsulfonyloxy, X is CH or N, $R^1$ is methyl, and $R^2$ and $R^3$ each are methyl or fluoromethyl.

Specifically, the following compounds may be mentioned:

N-(5-tert-butyl-1,3-oxazol-2-yl)-3,4-dimethyl-2-hydroxy-5-oxo-2,5dihydropyrrole;

N-(5-tert-butyl-1,3,4-oxadiazol-2-yl)-3,4-dimethyl-2-hydroxy-5-oxo-2,5-dihydropyrrole; and N-(5-tert-butyl-1,3,4-oxadiazol-2-yl)-2-chloro-3,4-dimethyl-5-oxo-2,5-dihydropyrrole.

If as starting materials in the process (a) there are employed, for example, N-(5-tert-butyl-1,3-oxazol-2-yl)-2,3-dimethyl maleinimide and sodium borohydride, the reaction can be expressed by the following formula:

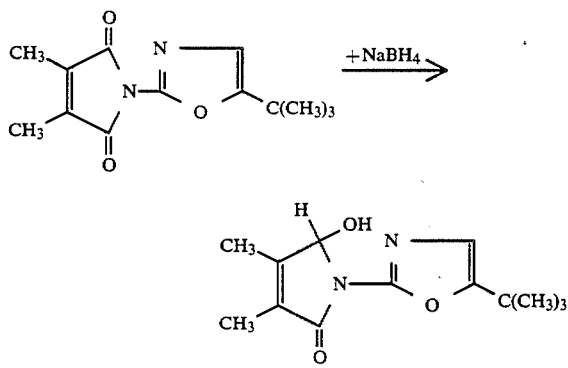

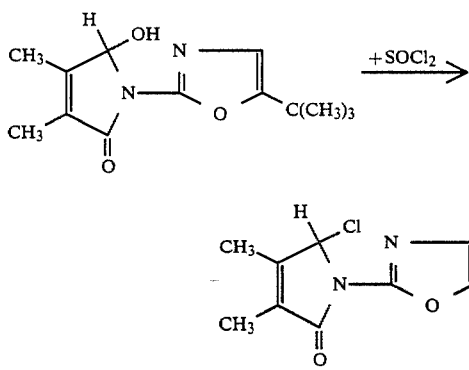

If as starting materials in the process (b) there are employed, for instance, N-(5-tert-butyl-1,3-oxazol-2-yl)-3,4-dimethyl-2-hydroxy-5-oxo-2,5-dihydropyrrole and thionyl chloride, the reaction can be expressed by the following formula:

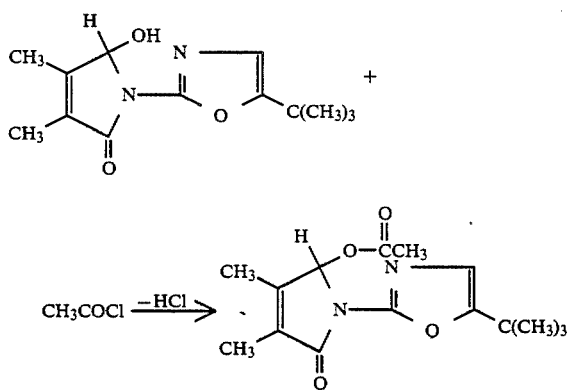

If as starting materials in the process (c) there are employed, for example, N-(5-tert-butyl-1,3-oxazol-2-yl)-3,4-dimethyl-2-hydroxy-5-oxo-2,5-dihydropyrrole and acetyl chloride, the reaction can be expressed by the following formula:

In the process (a), X, $R^1$, $R^2$ and $R^3$ in the formula (II) of the starting materials have respectively the same meaning as above.

Preferably, X, $R^1$, $R^2$ and $R^3$ in the formula (II) have respectively the same preferred meaning as stated before.

The compounds of the formula (II) are novel, and can be produced by reacting a compound of the formula:

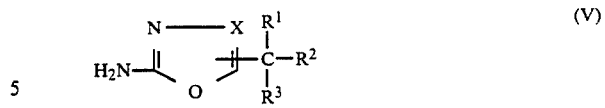

wherein X, $R^1$, $R^2$ and $R^3$ have respectively the same meaning as above, either with 2,3-dimethylmaleic anhydride or with 2 moles of maleic anhydride per mole of the compound of the formula (V).

Referring to the above-mentioned two methods for preparing the compounds of the formula (II), the former method can be carried out in the manner disclosed in Japanese Patent Laid-open No. 23965/1978, and the latter method can be conducted inthe manner shown in Japanese Patent Laid-open No. 46209/1977.

The 2-aminooxazoles where the group

in the formula (V), is attached to the 4- or 5-position can be prepared, according to a method described in Ann., vol. 467, p. 262 and Japanese Pharmacentical Journal, vol. 87, No. 1, p. 14, 1967 and ibid, vol. 91, No. 4, pp. 425 to 435, 1971.

The 2-amino-1,3,4-oxadiazoles where the group

in the formula (V), is attached to the 5-position can be prepared, according to a method described in U.S. Pat. No. 2,883,391, East German Patent No. 52,668 or Khim, Geterotsiki Soedin, vol. 11, pp. 1553 to 1556, 1986.

Alternatively, 2-amino-5-tert-butyl-1,3-oxazole, along with 2-amino-4-tert-butyl-1,3-oxazole can be obtained by reacting tert-butyl chloromethyl ketone with cyanamide.

In the above process, 2-amino-4-tert-butyl-1,3-oxazole can also be obtained, according to a method described in Aust. J. Chem., vol. 38, p. 447, 1985.

Examples of compounds of the formula (V) are 2-amino-4-tert-butyl-1,3-oxazole, 2-amino-5-tert-butyl-1,3-oxazole, and the like.

Examples of reducing aents, which can be employed in the process (a), are metal hydrides such as sodium borohydride, lithium aluminum hydride, and the like.

Examples of halogenating agents, which can be used in the process (b), are thionyl chloride and the like.

Referring to the starting compounds of the formulae (III) and (IV) employed in the process (c), the symbols W and M in the formulae have the meaning stated above. Preferably, W represents an alkylcarbonyl group having alkyl with 1 or 2 carbon atoms optionally substituted by fluorine and/or by chlorine, or an alkylsulfonyl group with 1 or 2 carbon atoms optionally substituted by fluorine and/or by chlorine, and M represents chlorine.

The compounds of the formulae (III) and (IV) include known compounds, such as acetyl chloride, methane sulfonyl chloride, trifluoroacetic anhydride, acetic anhydride, etc.

As appropriate diluents for carrying out the process (a), every kind of inert organic solvent may be mentioned.

Examples of the diluents are ethers such as dioxane and tetrahydrofuran; alcohols such as methanol, ethanol, isopropanol, butanol and ethylene glycol; acid amides such as N,N-dimethylformamide, and the like.

The reaction temperature of the process (a) may vary in a fairly wide range. In general, the reaction is carried out at a temperature of about −20° to +80° C., preferably a temperature of about 0° to 30° C.

It is preferred to carry out the reaction under the normal pressure, although a higher or lower pressure can also be used.

In carrying out the process (a), it is possible to subject the compounds of the formula (II) to a reducing reaction with the aid of a reducing agent as mentioned above, so that the aimed compounds of the formula (I) can be obtained as shown in the examples given below.

In carrying out the process (b), use may be made of appropriate diluents, including hydrocarbons such as benzene, toluene and xylene; halogenated hydrocarbons such as methylene chloride, chloroform, carbon tetrachloride, chlorobenzene, etc.

The process (b) may be carried out substantially within a wide range of temperatures. For instance, it may be carried out at a temperature, for example, of about −20° C. to 150° C., preferably about 0° C. to 80° C.

The reaction is preferably carried out under normal pressure, but it may be operated under a higher or a lower pressure.

In carrying out the process (b), it is possible to subject, for instance, the compounds of the formula (Ia) to a chlorination reaction with the aid of thionyl chloride, so that the aimed compounds of the formula (I) can easily be obtained.

In carrying out the process (c), use may be made of appropriate diluents, including, for instance, ethers such as dioxane and tetrahydrofuran; acid amides such as N,N-dimethylformamide, N,N-dimethylacetamide and hexmethylphosphoric triamide; sulfoxides such as dimethyl sulfoxide, and the like.

The process (c) may be conducted in the presence of an acid-binding agent. Examples of the acid-binding agents are alkali metal hydrides; tertiary amines such as triethylamine, diethylaniline, pyridine, 4-dimethylaminopyridine, 1,8-diazabicyclo[5,4,0]undec-7-ene (DBU), 1,4-diazabicyclo[2,2,2]octane (DABCO), and the like.

The process (c) may be carried out substantially within a wide range of temperatures. It may be carried out at a temperature, for example, within about 50° C.-200° C., preferably within about 80° C.-160° C.

The reaction is preferably carried out under normal pressure, but it may be operated under a higher or a lower pressure.

In conducting the process (c), about 1 to 1.5 moles of the compounds of formulae (III) or (IV) may be employed per mole of the compounds of the formula (Ia). These compounds may be reacted with each other in an inert solvent, optionally in the presence of an acid-binding agent, so that the aimed compounds of the formula (I) can be obtained.

The compounds of the formula (I) according to the invention have an asymmetric carbon atom in the 2-position of the 2,5-dihydropyrrole ring. Therefore, the 2,5-dihydropyrroles of the formula (I) according to the invention include the optical isomers.

The active compounds accordin to the invention can be used as defoliants, desiccants, agents for destroying broad-leaved palnts and, especially, as weedkillers. By weeds, in the broadest sense, there are to be understood all plants which grow in locations where they are undesired. Whether the substances according to the invention act as total or selective herbicides depends essentially on the amount used.

The active compouns according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be emplyed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the slective combating of weeds in annual cultures.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic, hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.0005 and 3 kg active compound per hectare of soil surface, preferably between 0.001 and 2 kg per ha.

The preparation and use of the active compounds according to the invention can be seen from the following examples.

PREPARATIVE EXAMPLES

Example 1

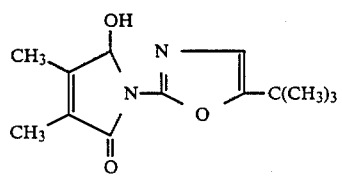

A mixture of 2-amino-5-tert-butyl-1,3-oxazole (1.40 g) and 2,3-dimethylmaleic anhydride (1.51 g) was heated in toluene (30 ml) under reflux for 2 hours. The water formed during the reactio was removed by means of a Dean-Stark device. Then acetic acid (5 ml) was added, and the reaction mixture was further heated for 2 hours. After the completion of the reaction, the solvent and the excess acid anhydride were removed under reduced pressure. The residue was dissolved in methanol (50 ml), and sodium borohydride (0.38 g) was added in increments at room temperature. Thereafter, the reaction mixture was stirred at room temperature for 3 hours. After this reaction, acetic acid (0.5 ml) was added, and the solvent was distilled off under a reduced pressure. The residue was admixed with water, rendered alkaline with potassium carbonate, and extracted with methylene chloride (50 ml×2). After the reaction mixture was dried over anhydrous magnesium sulfate, the solvent was removed under reduced pressure, and the residue was recrystallized from hexane, so that the desired compound, i.e. N-(5-tert-butyl-1,3-oxazol-2-yl)-3,4-dimethyl-2-hydroxy-5-oxo-2,5-dihydropyrrole (2.15 g), was obtained. mp. 103°–104° C.

Example 2

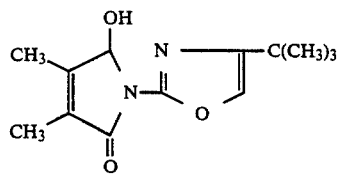

2-Amino-4-tert-butyl-1,3-oxazole (1.40 g), 2,3-dimethylmaleic anhydride (1.51 g) and sodium borohydride (0.38 g) were reacted in a manner similar to that shown in Example 1. The resulting product was recrystallized from a toluene/hexane mixture, so that the desired compound, i.e. N-(4-tert-butyl-1,3-oxazol-2-yl)-3,4-dimethyl-2-hydroxy-5-oxo-2,5-dihydropyrrole (2.10 g), was obtained. mp. 171°–174° C.

In the same manner as in the preceding examples, a number of the compounds according to the invention can be prepared. These compounds as well as the compounds prepared in Examples 1 and 2 are shown in Table 1.

TABLE 1

| Compound No. | A | N—X, C(R¹)(R²)(R³) group | Physical constant |
|---|---|---|---|
| 1 | —OH | N=C(CH₃)—O—CH=CH—C(CH₃)₃ | mp. 171–174° C. |
| 2 | —OCOCH₃ | N=C(CH₃)—O—CH=CH—C(CH₃)₃ | $n_D^{50}$ 1.4955 |
| 3 | —OCOCF₃ | N=C(CH₃)—O—CH=CH—C(CH₃)₃ | $n_D^{50}$ 1.485 |
| 4 | —OSO₂CH₃ | N=C(CH₃)—O—CH=CH—C(CH₃)₃ | $n_D^{20}$ 1.4980 |
| 5 | —Cl | N=C(CH₃)—O—CH=CH—C(CH₃)₃ | Viscous oil |
| 6 | —OH | N=C(CH₃)—O—CH=C(C(CH₃)₃) | mp. 103–104° C. |
| 7 | —OCOCH₃ | N=C(CH₃)—O—CH=C(C(CH₃)₃) | mp. 96–101° C. |
| 8 | —Cl | N=C(CH₃)—O—CH=C(C(CH₃)₃) | Viscous oil |
| 9 | —OH | N=C(CH₃)—O—CH=CH—C(CH₃)₂CH₂F | |
| 10 | —OH | N=C(CH₃)—O—CH=CH—C(CH₃)(CH₃F)(CH₂F) | |
| 11 | —OH | N=C(CH₃)—O—CH=C(C(CH₃)₂CH₂F) | |
| 12 | —OH | N=C(CH₃)—O—CH=C(C(CH₃)(CH₂F)₂) | |

TABLE 1-continued

General structure (top):
5-membered ring with CH₃, CH₃, H, A substituents, connected via N–C(=O)–N—X with C(R¹)(R²)(R³).

| Compound No. | A | [N—X side group] | Physical constant |
|---|---|---|---|
| 13 | —OH | N=N, with C(CH₃)₃ (oxadiazole-type, O in ring) | mp. 142–144° C. |
| 14 | —OCOCH₃ | same ring, C(CH₃)₃ | $n_D^{50}$ 1.4935 |
| 15 | —OCOCF₃ | same ring, C(CH₃)₃ | $n_D^{50}$ 1.485 |
| 16 | —OSO₂CH₃ | same ring, C(CH₃)₃ | $n_D^{50}$ 1.5025 |
| 17 | —Cl | same ring, C(CH₃)₃ | mp. 112–116° C. |
| 18 | —Br | same ring, C(CH₃)₃ | mp. 94–98° C. |
| 19 | —OH | same ring, C(CH₃)₂C₂H₅ | |
| 20 | —OH | same ring, C(CH₃)(C₂H₅)₂ | |
| 21 | —OH | same ring, C(CH₂)₂CH₂F | |
| 22 | —OH | same ring, C(CH₃)(CH₂F)₂ | |
| 23 | —OH | same ring, C(CH₃)₂CH₂Cl | |
| 24 | —OH | same ring, cyclopropyl-CH₃ | |

BIOTEST EXAMPLES

Known comparison compound employed:

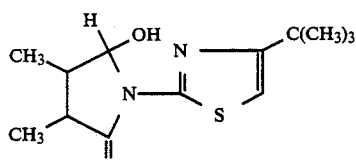

(E-1)

disclosed in Japanese Patent Laid-opne No. 23965/1978)

Example 3

Pre-emergence test/weeds in upland crop fields/soil treatment

Formulation of Active Compounds

Carrier: 5 parts by weight of acetone
Emulsifier: 1 part by weight of benzyloxy polyglycol ether A formulation of an active compound was obtained as an emulsifiable concentrate by mixing 1 part by weight of the active compound with the above-mentioned amounts of the carrier and the emulsifying agent. A predetermined amount of the formulation was diluted with water.

Testing method

In a greenhouse, corn seeds were sown in 500 cm² pots filled with upland farm soil, and soil containing seeds of barnyard grass (*Echinochloa crus-galli*), Digitaria (*Digitaria sanguinalis*), livid amaranth (*Amaranthus lividus* L.) and goosefoot (*Chenopodium album* L.) was put over the soil in the pots in a depth of 1 cm.

One day after sowing, a test chemical in a predetermined concentration was uniformly sprayed over the surface layer of the soil in each of the test pots.

Four weeks after the spraying, the herbicidal effect and the phytotoxicity to crops were evaluated and rated on the scale of 0 to 5 as follows:

Herbicidal effect (evaluated by a weed killing ratio based on a non-treated lot):
5: at least 95% (withered)
4: at least 80% but less than 95%
3: at least 50% but less than 80%
2: at least 30% but less than 50%
1: at least 10% but less than 30%
0: less than 10% (no effect)

Phytotoxicity to crop (evaluated based on a non-treated lot):
5: at least 90% (fatal injury)
4: at least 50% but less than 90%
3: at least 30% but less than 50%
2: at least 10% but less than 30%
1: more than 0 but less than 10%
0: 0% (no phytotoxicity)

The test results are shown in Table 2.

TABLE 2

| Active compound | Amount of active compound (kg/ha) | Herbicidal effect on weeds | | | | Phytotoxic effect on corn plants |
|---|---|---|---|---|---|---|
| | | Barnyard grass | Digitaria | Livid amaranth | Goosefoot | |
| 6 | 0.5 | 5 | 5 | 5 | 5 | 1 |
| | 0.25 | 4 | 5 | 5 | 5 | 0 |
| 7 | 0.5 | 5 | 5 | 5 | 5 | 1 |
| | 0.25 | 4 | 5 | 5 | 5 | 0 |
| 13 | 0.5 | 4 | 5 | 5 | 5 | 0 |
| | 0.25 | 4 | 4 | 5 | 5 | 0 |
| (Known compound) | | | | | | |
| E-1 | 0.5 | 1 | 1 | 2 | 1 | 0 |
| | 0.25 | 0 | 0 | 0 | 0 | 0 |

Example 4

Test on upland farm weeds by foliar treatment

In a greenhouse, corn seeds were sown in 500 cm² pots filled with upland farm soil, and soil containing seeds of Digitaria (*Digitaria sanguinalis*), livid amaranth (*Amaranthus lividus* L.) goosefoot (*Chenopodium album* L.) and purslane (*Portulaca oleracea* L.) was put over the soil in the pots in a depth of 1 cm.

After sowing, the plants were grown for 14 days and a test chemical in a predetermined concentration, prepared as in Example 3, was uniformly sprayed over the test plants in each of the test pots.

Four weeks after the spraying, the herbicidal effect and the phytotoxicity to crops were examined on the same standards as in Example 3. The results are shown in Table 3.

TABLE 3

| Active compound | Amount of active compound (kg/ha) | Herbicidal effect on weeds | | | | Phytotoxic effect on corn plants |
|---|---|---|---|---|---|---|
| | | Digitaria | Livid amaranth | Goosefoot | Purslane | |
| 6 | 0.5 | 5 | 5 | 5 | 5 | 0 |
| | 0.25 | 5 | 5 | 5 | 5 | 0 |
| 13 | 0.5 | 5 | 5 | 5 | 5 | 0 |
| | 0.25 | 5 | 5 | 5 | 5 | 0 |

TABLE 3-continued

| | Amount of active compound (kg/ha) | Herbicidal effect on weeds | | | | Phytotoxic effect on corn plants |
| --- | --- | --- | --- | --- | --- | --- |
| | | Digitaria | Livid amaranth | Goosefoot | Purslane | |
| 17 (Known compound) | 0.5 | 5 | 5 | 5 | 5 | 1 |
| | 0.25 | 5 | 5 | 5 | 5 | 0 |
| E-1 | 0.5 | 1 | 2 | 2 | 1 | 0 |
| | 0.25 | 0 | 1 | 1 | 0 | 0 |

It will be appreciated that the instant specification and claims are set forth by way of illustration and not limitation, and that various modifications and changes may be made without departing from the spirit and scope of the present invention.

What is claimed is:

1. A 2,5-dihydropyrrole of the formula

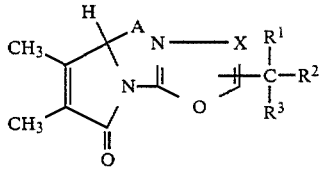

wherein

A represents hydroxy, halogen, an alkylcarbonyloxy group having alkyl with 1 to 4 carbon atoms optionally substituted by halogen, or an alkylsulfonyloxy group having 1 to 4 carbon atoms optionally substituted by halogen, X represents CH or N, and $R^1$, $R^2$ and $R^3$ each represent hydrogen, or an alkyl group having 1 to 4 carbon atoms optionally substituted by halogen, with the proviso that all of $R^1$, $R^2$ and $R^3$ do not simultaneously represent hydrogen, or $R^2$ and $R^3$, together with the carbon atom to which they are bonded, may form an alicyclic ring with 3 to 6 carbon atoms.

2. A compound according to claim 1, in which

A represents hydroxy, chlorine, bromine, an alkoxycarbonyloxy having alkyl with 1 or 2 carbon atoms optionally substituted by fluorine and/or by chlorine, or an alkylsulfonyloxy having 1 or 2 carbon atoms optionally substituted by fluorine and/or by chlorine, X represents CH or N, $R^1$ represents methyl or ethyl, and $R^2$ and $R^3$ each represent methyl, ethyl, or chlorine- or fluorine-substituted alkyl with 1 or 2 carbon atoms, or $R^2$ and $R^3$, together with the carbon atoms to which they are bonded, may form a cyclopropane ring.

3. A compound according to claim 1, in which

A represents hydroxy, chlorine, bromine, acetyloxy, trifluoroacetyloxy or methylsulfonyloxy, X is CH or N, $R^1$ is methyl, and $R^2$ and $R^3$ each are methyl or fluoromethyl.

4. A compound according to claim 1, wherein such compound is N-(5-tert-butyl-1,3-oxazol-2-yl)-3,4-dimethyl-2-hydroxy-5-oxo-2,5-dihydropyrrole of the formula

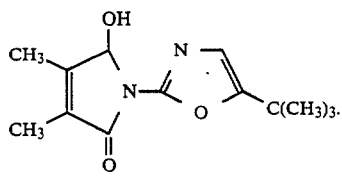

5. A compound according to claim 1, wherein such compound is N-(5-tert-butyl-1,3-oxazol-2-yl)-3,4-dimethyl-2-acetoxy-5-oxo-2,5-dihydropyridine of the formula

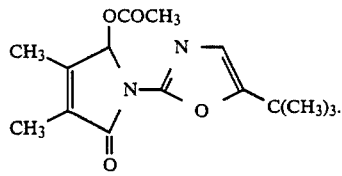

6. A compound according to claim 1, wherein such compound is N-(5-tert-butyl-1,3,4-oxadiazol-2-yl)-3,4-dimethyl-2-hydroxy-5-oxo-2,5-dihydropyrrole of the formula

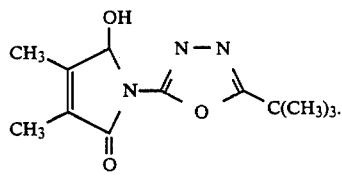

7. A compound according to claim 1, wherein such compound is N-(5-tert-butyl-1,3,4-oxadiazol-2-yl)-2-chloro-3,4-dimethyl-5-oxo-2,5-dihydropyrrole of the formula:

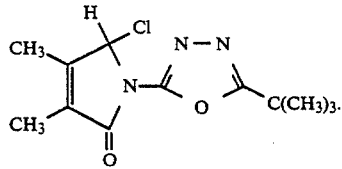

8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidally effective amount of a compound according to claim 1.

10. The method according to claim 9, wherein such compound is

N-(5-tert-butyl-1,3-oxazol-2-yl)-3,4-dimethyl-2-hydroxy-5-oxo-2,5-dihydropyrrole, N-(5-tert-butyl-1,3-oxazol-2-yl)-3,4-dimethyl-2-acetoxy-5-oxo-2,5-dihydropyridine, N-(5-tert-butyl-1,3,4-oxadiazol-2-yl)-3,4-dimethyl-2-hydroxy-5-oxo-2,5-dihydropyrrole, or N-(5-tert-butyl-1,3,4-oxadiazol-2-yl)-2-chloro-3,4-dimethyl-5-oxo-2,5-dihydropyrrole.

11. A compound of the formula

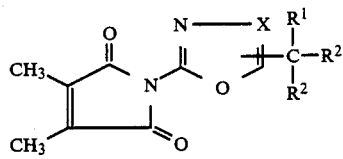

(II)

in which
X represents CH or N, and
$R^1$, $R^2$ and $R^3$ each represent hydrogen, or an alkyl group having 1 to 4 carbon atoms optionally substituted by halogen, with the proviso that all of $R^1$, $R^2$ and $R^3$ do not simultaneously represent hydrogen,
or $R^2$ and $R^3$, together with the carbon atom to which they are bonded, may form an alicyclic ring with 3 to 6 carbon atoms.

* * * * *

UNITED STATES PATENT AND TRADEMARK OFFICE
CERTIFICATE OF CORRECTION

PATENT NO. : 4,909,828

DATED : March 20, 1990

INVENTOR(S) : Kume et al.

It is certified that error appears in the above-identified patent and that said Letters Patent is hereby corrected as shown below:

Title Page: [75] inventors: After " Kume, " delete " Hino; " after " Goto, " delete " Machida; " after " Kamochi, " delete " Hino; "after Yanagi," delete " Oume; " after " Miyauchi, " delete " Hachioji, all of Japan " and substitute -- all of Tokyo, Japan --

Col. 15, claim 2 lines 46-47 Delete " alkoxycarbonyloxy " and substitute -- alkylcarbonyloxy --

Col. 15, claim 2 line 57 Delete " atoms " and substitute -- atom --

Signed and Sealed this

Twenty-second Day of October, 1991

Attest:

HARRY F. MANBECK, JR.

Attesting Officer  Commissioner of Patents and Trademarks